United States Patent [19]

Kline

[11] 3,989,738
[45] Nov. 2, 1976

[54] METHOD OF PREPARING PHENOLIC ANTIOXIDANTS BY CONDENSING ACTIVE METHYLENE COMPOUNDS WITH 3,5-DI-TERT ALKYL-4-HYDROXYBENZYLPYRIDINIUM SALTS

[75] Inventor: Richard H. Kline, Cuyahoga Falls, Ohio

[73] Assignee: The Goodyear Tire & Rubber Company, Akron, Ohio

[22] Filed: July 21, 1975

[21] Appl. No.: 597,803

[52] U.S. Cl. .......................... 260/473 S; 260/290 P; 260/290 HL; 260/465 F; 260/592; 260/622 R
[51] Int. Cl.$^2$ .................. C07C 69/76; C07C 49/82; C07C 79/22; C07C 121/50
[58] Field of Search ............. 260/473 S, 465 F, 592, 260/622 R

[56] References Cited
UNITED STATES PATENTS 3,678,095  7/1972  Dexter et al. .................... 260/473 S Primary Examiner—Paul J. Killos
Attorney, Agent, or Firm—F. W. Brunner; J. A. Rozmajzl

[57] ABSTRACT

3,5-Di-tert alkyl-4-hydroxybenzylpyridinium salts are reacted under basic conditions with compounds containing active methylene groups to form phenolic antioxidants. For example, 3,5-di-tert.butyl-4-hydroxybenzylpyridinium chloride is reacted with 2-nitropropane to produce 1,1-dimethyl-2-(3,5-di tert.butyl-4-hydroxyphenyl)-1-nitroethane.

4 Claims, No Drawings

METHOD OF PREPARING PHENOLIC ANTIOXIDANTS BY CONDENSING ACTIVE METHYLENE COMPOUNDS WITH 3,5-DI-TERT ALKYL-4-HYDROXYBENZYLPYRIDINIUM SALTS

This invention relates to the preparation of phenolic antioxidants by reacting 3, 5-di-tert. alkyl-4-hydroxybenzylpyridinium salts with compounds containing active methylene groups.

Various phenolic antioxidants and their preparation are described in the prior art. Some of the compounds are described in U.S. Pat. No. 3,867,467; Netherlands Patent No. 6,711,199; Netherlands Patent No. 6,803,498 (U.S. Pat. No. 3,646,110); French Patent No. 1,536,020 (U.S. Pat. No. 3,627,725); and French Patent No. 1,564,677 (U.S. Pat. No. 3,678,095). Alternate methods of preparing phenolic antioxidants can be advantageous.

It is an object of the present invention to provide a method of preparing phenolic antioxidants. Other objects will become apparent as the description proceeds.

The objects of the present invention are accomplished by a reaction involving the condensation of compounds containing methylene groups with 3,5-di-tert alkyl-4-hydroxybenzylpyridinium salts in the presence of a base.

The pyridinium salts have the following structural formula I:

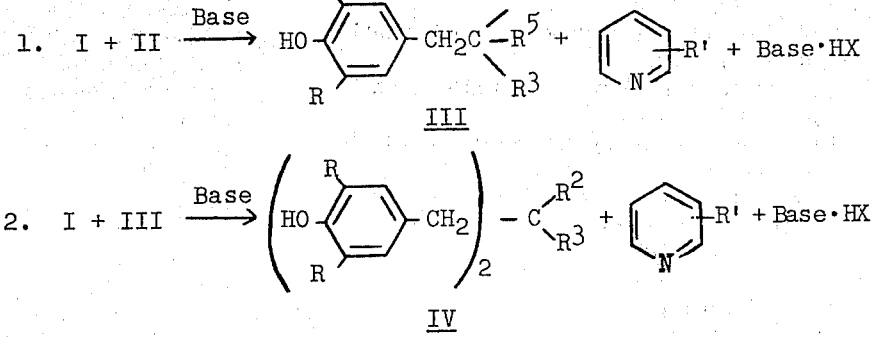

wherein R is a tertiary alkyl radical having 4 to 8 carbon atoms, $R^1$ is selected from the group consisting of hydrogen, methyl and ethyl and X is a hologen radical selected from the group consisting of chloro, bromo and iodo.

The active methylene compounds which can be reacted with the compounds of structural formula I are represented by the following structural formula II:

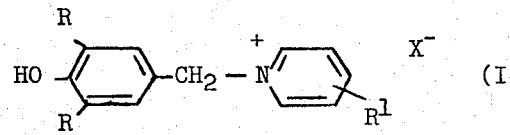

wherein $R^5$ is selected from the group consisting of hydrogen and alkyl radicals containing 1 to 4 carbon atoms, and wherein $R^2$ and $R^3$ are selected from the group consisting of $-COOR^4$, $-COR^4$, $-CN$ and $-NO_2$, wherein $R^4$ is an alkyl radical containing from 1 to 4 carbon atoms, with the proviso that when $R^2$ is $NO_2$, $R^3$ can also be hydrogen or an alkyl radical containing 1 to 4 carbon atoms.

The reaction between the compounds of structural formulae I and II can be represented by the following equations. Reaction number 2 will naturally occur only when $R^5$ is hydrogen.

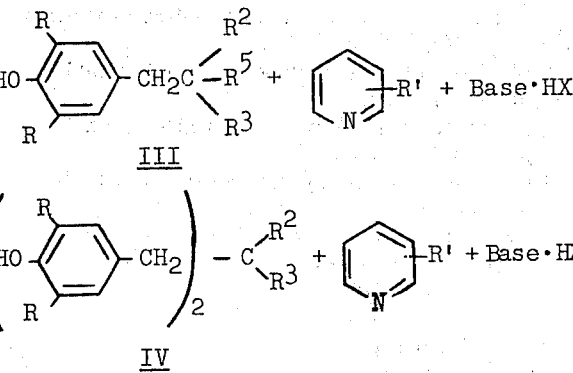

Compounds of the structures III and IV can be used as antioxidants in rubbers and other compositions susceptible to oxidative degradation.

The base can be any typical base used in condensation reactions; for example, an alkali metal alkoxide such as sodium methoxide, sodium ethoxide or potassium tertiary butoxide; a tertiary amine such as trimethyl amine, triethyl amine or N-methyl pyrrolidine or, when the active methylene compound does not contain an ester group, an alkali metal hydroxide such as socium hydroxide or potassium hydroxide can be used.

The molar ratio of I to II is from 2.5/1 to 1/10. Either the monobenzyl (structural formula III) or the bisbenzyl (structural formula IV) derivatives of the active methylene compounds can be obtained as the principal product of the reaction depending upon the relative amounts of compounds I and II which are charged. Using a molar ratio of 1/1 to 1/10, preferably 1/2 to 1/3, will result in higher yields of the compound of structural formula III while a molar ratio of from 2/1 to 2.5/1, 2/1 preferred, will yield principally the compound of structural formula IV.

The pyridinium salts can be prepared by the gradual addition of a 3,5-di-tert alkyl-4-hydroxybenzyl halide to a solution of an equivalent amount of pyridine or an alkyl substituted pyridine in acetone. The addition is accomplished at ambient temperatures. The product which precipitates during the reaction is filtered off and allowed to dry.

The active methylene compounds and bases are all well known in the art.

Aliphatic alcohols, such as ethanol or 2-propanol, are the preferred solvents for this reaction, although other polar solvents such as diethyl ether, tetrahydrofuran, N,N-dimethylformamide and dimethyl sulfoxide can be used.

Preferably the reaction temperature approximates room temperature, that is, from 20° to 30° C. However, the reaction temperature can be from 0° to the boiling point of the solvent, although preferably no higher than 100° C.

Compounds of structural formulae I, II, III and IV are illustrated by but not limited to the following.

I 3,5-di-tert.butyl-4-hydroxybenzylpyridinium chloride
3,5-di-tert.butyl-4-hydroxybenzylpyridinium bromide
3,5-bis (1,1-dimethylbutyl)-4-hydroxybenzyl-pyridinium chloride
3,5-di-tert.butyl-4-hydroxybenzylpyridinium iodide
3,5-bis (1,1,3-trimethylbutyl)-4-hydroxybenzyl-pyridinium chloride
1-(3,5-di-tert.butyl-4-hydroxybenzyl)-2-methyl-pyridinium chloride
1-(3,5-di-tert.butyl-4-hydroxybenzyl)-3-methyl-pyridinium chloride
1-(3,5-di-tert-butyl-4-hydroxybenzyl)-4-methyl-pyridinium chloride
1-(3,5-di-tert-butyl-4-hydroxybenzyl)-4-ethyl-pyridinium chloride

II dimethyl malonate
diethyl malonate
2,4-pentanedione
methyl acetoacetate
ethyl acetoacetate
ethyl cyanoacetate
nitroethane
1-nitropropane
2-nitropropane
nitromethane
diethyl methylmalonate

III diethyl 2-(3,5-di-tert.butyl-4-hydroxybenzyl)malonate
dimethyl 2-(3,5-di-tert.butyl-4-hydroxybenzyl) malonate
ethyl 2-(3,5-di-tert.butyl-4-hydroxybenzyl)acetoacetate
3-(3,5-di-tert.butyl-4-hydroxybenzyl)-2,4-pentanedione
ethyl 2-(3,5-di-tert.butyl-4-hydroxybenzyl) cyanocacetate
1-methyl-2-(3,5-di-tert.butyl-4-hydroxyphenyl)-1-nitroethane
1-ethyl-2-(3,5-di-tert.butyl-4-hydroxyphenyl)-1-nitroethane
1,1-dimethyl-2-(3,5-di-tert.butyl-4-hydroxyphenyl)-1-nitroethane

IV diethyl 2,2-bis(3,5-di-tert.butyl-4-hydroxybenzyl) malonate
ethyl 2,2-bis(3,5-di-tert.butyl-4-hydroxybenzyl) acetoacetate
methyl 2,2-bis(3,5-di-tert.butyl-4-hydroxybenzyl) cyanoacetate
3,3-bis(3,5-di-tert.butyl-4-hydroxybenzyl)-2,4-pentanedione
bis (3,5-di-tert.butyl-4-hydroxybenzyl) nitromethane
1,1-bis (3,5-di-tert.butyl-4-hydroxybenzyl) nitroethane
1,1-bis(3,5-di-tert.butyl-4-hydroxybenzyl)-1-nitropropane Preferably R is a tert.butyl radical, $R^1$ is hydrogen, X is Cl, $R^2$ is $COOR^4$ or $NO_2$, $R^3$ or $COOR^4$ or $CH_3$, $R^4$ is $CH_3$ or $C_2H_5$ and $R^5$ is hydrogen or $CH_3$.

The method of the present invention is normally run at or above atmospheric pressure. The method may be accomplished in batch or continuous form.

The reaction can be carried out by combining an alcohol solution of a 3,5-di-tert alkyl-4-hydroxybenzyl-pyridinium salt with a solution or slurry of the active methylene compound and an equivalent amount of a base in an alcohol. The base may be an alkali metal hydroxide or alcoholate or a tertiary aliphatic amine. The reaction is carried out at ambient temperature, and the reaction mixture is stirred for a period of up to 3 hours after the addition is complete. The product is isolated by pouring the reaction mixture into a large volume of water and separating the precipitated product by extraction or filtration or other suitable means. The product may be purified by recrystallization if desired. This general description is only intended to include guidelines and should not be considered to be limiting.

Examples 1 to 4 illustrate, but do not limit the preparation of pyridinium salts used in the practice of the present invention.

EXAMPLE 1

127½ Grams of 3,5-di-tert.butyl-4-hydroxybenzyl chloride was added dropwise, in 40 minutes, to a solution of 44.0 grams of pyridine in 500 milliliters of acetone. The mixture was stirred briefly and was then filtered, yielding 159 grams of 3,5-di-tert.butyl-4-hydroxybenzyl-pyridinium chloride, with a melting point of 239°–240° C. (with decomposition). This represents 95 percent of theory.

EXAMPLE 2

3,5-di-tert.butyl-4-hydroxyybenzyl-3-methyl-pyridinium chloride was prepared by adding 25.5 grams of 3,5-di-t-butyl-4-hydroxybenzyl chloride to a solution of 9.3 grams of 3-picoline in 100 milliliters of acetone. The addition was completed in 15 minutes and the mixture was filtered yielding 33 grams of product melting at 222°–223° C. (with decomposition). This also represents 95 percent of theory.

EXAMPLE 3

3,5-di-tert.butyl-4-hydroxybenzyl-2-methyl-pyridinium chloride was obtained in 96.5 percent yield when 2-picoline was substituted for 3-picoline in the procedure described in the previous example. This compound melted at 195°–196° C. (with decomposition).

EXAMPLE 4

A solution of 9.3 grams of a mixture consisting of 85 percent 4-picoline and 15 percent 3-picoline in 100 milliliters of acetone had added to it 25.5 grams of 3,5-di-tert.butyl-4-hydroxybenzyl chloride. The addition was completed in 15 minutes and the mixture was filtered yielding 34 grams of a mixture of 3,5-di-tert.butyl-4-hydroxybenzyl-3- and 4-methyl-pyridinium chlorides which melted at 215°–218° C. (with decomposition). This represents 98 percent of theory.

Examples 5 to 15 illustrate, but do not limit, the process of the present invention.

EXAMPLE 5

A solution of 15.8 grams of 3,5-di-tert.butyl-4-hydroxybenzylpyridinium chloride in 50 milliliters of ethanol was added in 40 minutes to a solution of 4.45 grams of 2-nitropropane and 2.0 grams of sodium hydroxide in 50 milliliters of ethanol. The temperature rose during the addition from 27° to 31° C. The reaction mixture was stirred for 2½ hours and was then poured into 400 milliliters of water. The solid which precipitated was filtered off and allowed to dry. The yield of crude 1,1-dimethyl-2-(3,5-di-tert.butyl-4-hydroxyphenyl)-1-nitroethane was 14.0 grams (96.5% of theory). This compound has a melting point of 100°-102° C. (from hexane).

EXAMPLE 6

15.3 Grams (100% of theory) of 1,1-dimethyl-2-(3,5-di-tert.butyl-4-hydroxyphenyl)-1-nitroethane was obtained when 17.4 grams of 3,5-di-tert.butyl-4-hydroxybenzyl-3-methylpyridinium chloride was substituted for the pyridinium salt of Example 5.

EXAMPLE 7

Substitution of 17.4 grams of 3,5-di-tert.butyl-4-hydroxybenzyl-2-methylpyridinium chloride for the pyridinium salt of Example 5 yielded 15.0 grams (98% of theory) of 1,1-dimethyl-2-(3,5-di-tert.butyl-4-hydroxyphenyl)-1-nitroethane.

EXAMPLE 8

Use of 17.4 grams of the mixture of 3- and 4-methylpyridinium salts produced in Example 4 in place of the pyridinium salt of Example 5 yielded 15.0 grams (98% of theory) 1,1-dimethyl-2-(3,5-di-tert.butyl-4-hydroxyphenyl)-1-nitroethane.

EXAMPLE 9

A solution of 16.7 grams of 3,5-di-tert.butyl-4-hydroxybenzylpyridinium chloride in 50 milliliters of ethanol was added dropwise in 15 minutes to a slurry of 2.0 grams of sodium hydroxide and 13.4 grams of 1-nitropropane (200% excess) in 50 milliliters of ethanol. The reaction mixture as stirred for 3 hours and was then poured into 600 milliliters of water. The oil which precipitated was separated by extraction with hexane. The extract was evaporated to give 15.0 grams (98% of theory) of 1-ethyl-2-(3,5-di-tert.butyl-4-hydroxyphenyl)-1-nitroethane which melted at 55°-60° C.

EXAMPLE 10

When 11.25 grams of nitroethane was substituted for 1-nitropropane in the procedure of Example 9, a yield of 14.5 grams (99% of theory) of 1-methyl-2-(3,5-di-tert.butyl-4-hydroxyphenyl)-1-nitroethane was obtained. The product melted at 67°-71° C.

EXAMPLE 11

A solution of 33 grams of 3,5-di-tert.butyl-4-hydroxybenzylpyridinium chloride in 150 milliliters of ethanol was added dropwise in 45 minutes to a slurry of 4.0 grams of sodium hydroxide and 3.75 grams of nitroethane in 100 milliliters of ethanol. The reaction mixture was stirred for 3 hours and was then poured into 1 liter of water. The solid which precipitated was filtered off and allowed to dry. The crude product, which weighed 20 grams, was washed with hot ethanol yielding 10 grams of 1,1-bis(3,5-di-tert.butyl-4-hydroxybenzyl) nitroethane having a melting point of 203°-205° C.

EXAMPLE 12

A solution of 16.7 grams of 3,5-di-tert.butyl-4-hydroxybenzylpyridinium chloride in 50 milliliters of ethanol was added dropwise in 33 minutes to a solution of 5.05 grams of triethyl amine and 3.05 grams of nitromethane in 50 milliliters of ethanol. The reaction mixture was stirred for 6½ hours and was then poured into 400 milliliters of water. The solid which precipitated was filtered off, allowed to dry, and recrystallized from ethanol. The yield of bis(3,5-di-tert.butyl-4-hydroxybenzyl)nitromethane, having a melting point of 160°-163° C., was 8.6 grams.

EXAMPLE 13

Two and three tenths grams of sodium was dissolved in 100 milliliters of absolute ethanol and 32 grams of diethyl malonate was added. This solution was added dropwise in 20 minutes to a solution of 33 grams of 3,5-di-tert.butyl-4-hydroxybenzylpyridinium chloride in 150 milliliters of absolute ethanol. The reaction mixture was stirred for 1½ hours and was then poured into 1 liter of water. The oil which precipitated was separated by extraction with hexane. Hexane was removed from the extract by evaporation under aspirator vacuum and excess diethyl malonate was removed from the residue by distillation, also under aspirator vacuum. The viscous residue was dissolved in hexane and the solution was cooled with dry ice. The solid which crystallized out was filtered off and allowed to dry. The yield of diethyl 3,5-di-tert.butyl-4-hydroxybenzyl malonate was 21.5 grams. The product melted at 45°-48° C.

EXAMPLE 14

Eight grams of diethyl malonate was added to a solution of 2.3 grams of sodium in 100 milliliters of absolute alcohol and the resulting solution was added dropwise in 15 minutes to a solution of 33 grams of 3,5-di-tert.butyl-4-hydroxybenzylpyridinium chloride in 150 milliliters of absolute alcohol. The reaction mixture was stirred for 3 hours and was then poured into 1 liter of water. The solid which precipitated was filtered off, allowed to dry, and recrystallized from hexane. The yield of diethyl bis (3,5-di-tert.butyl4-hydroxybenzyl) malonate was 16.0 grams. The product melted at 155°-158° C.

EXAMPLE 15

Addition of 15 grams of acetyl acetone to a solution of 2.0 grams of sodium hydroxide in 50 milliliters of ethanol brought about the formation of a slurry which was added over a period of 20 minutes to a solution of 16.7 grams of 3,5-di-tert.butyl-4-hydroxybenzylpyridinium chloride in 50 milliliters of ethanol. The reaction mixture was stirred for 2½ hours and was then poured into 600 milliliters of water. The pale yellow oil which precipitated crystallized on standing overnight. The solid was filtered off and, after drying, weighed 15.2 grams. The 3-(3,5-di-tert.butyl-4-hydroxybenzyl)-2,4-pentanedione thus obtained melted at 77°-80° C. after recrystallization from petroleum ether.

All of the products of the method of the present invention are antioxidants.

Any of the aforementioned reactants, solvents, or bases could have been substituted in the previously described working examples to prepare phenolic antioxidants.

While certain representative embodiments and details have been shown for the purpose of illustrating the invention, it will be apparent to those skilled in this art that various changes and modifications may be made therein without departing from the spirit or scope of the invention.

What is claimed is:

1. A process of producing a phenolic antioxidant comprising reacting in solution, in the presence of a base, a combination comprised of a pyridinium salt having the structure

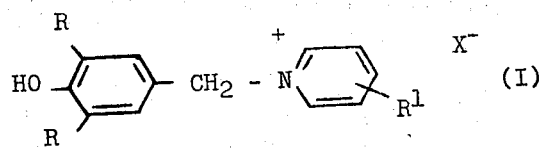

and an active methylene compound having the structure

wherein R is a tertiary alkyl radical having 4 to 8 carbon atoms, $R^1$ is selected from the group consisting of hydrogen, methyl and ethyl and X is a halogen radical selected from the group consisting of chloro, bromo and iodo, wherein $R^5$ is selected from the group consisting of hydrogen and alkyl radicals containing 1 to 4 carbon atoms, and wherein $R^2$ and $R^3$ are selected from the group consisting of $-COOR^4$, $-COR^4$, $-CN$ and $-NO_2$, wherein $R^4$ is an alkyl radical containing from 1 to 4 carbon atoms, with the proviso that when $R^2$ is $NO_2$, $R^3$ can also be hydrogen or an alkyl radical containing 1 to 4 carbon atoms, wherein the reaction temperature is from 0° C. to the boiling point of the solvent and wherein the molar ratio of I to II is from 2.5/1 to 1/10.

2. The process according to claim 1 wherein R is a tert.butyl radical, $R^1$ is hydrogen, X is Cl, $R^2$ is $COOR^4$ or $NO_2$, $R^3$ is $COOR^4$ or $CH_3$, $R^4$ is $CH_3$ or $C_2H_5$ and $R^5$ is hydrogen or $CH_3$.

3. The process according to claim 1 wherein the molar ratio of I to II is from 1/2 to 1/3.

4. The process according to claim 1 wherein the molar ratio of I to II is from 2/1 to 2.5/1.

* * * * *